(12) United States Patent
Mertins et al.

(10) Patent No.: US 12,097,024 B2
(45) Date of Patent: Sep. 24, 2024

(54) PROCESS, PORTABLE DEVICE AND SYSTEM FOR ANALYZING VECTOR DATA

(71) Applicant: Drägerwerk AG & Co. KGaA, Lübeck (DE)

(72) Inventors: Alfred Mertins, Lübeck (DE); Marco Maass, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 657 days.

(21) Appl. No.: 17/426,997

(22) PCT Filed: Mar. 29, 2019

(86) PCT No.: PCT/EP2019/057974
§ 371 (c)(1),
(2) Date: Jul. 29, 2021

(87) PCT Pub. No.: WO2020/156686
PCT Pub. Date: Aug. 6, 2020

(65) Prior Publication Data
US 2022/0142506 A1   May 12, 2022

(30) Foreign Application Priority Data
Jan. 30, 2019 (DE) ..................... 10 2019 000 608.9

(51) Int. Cl.
*A61B 5/113*    (2006.01)
*A61B 5/0205*   (2006.01)

(52) U.S. Cl.
CPC ............ *A61B 5/113* (2013.01); *A61B 5/0205* (2013.01)

(58) Field of Classification Search
CPC ...... A61B 5/113; A61B 5/0205; G16H 50/70; G16H 20/40
See application file for complete search history.

(56) References Cited

U.S. PATENT DOCUMENTS

| 6,580,944 B1 | 6/2003 | Katz et al. |
| 9,510,755 B2 | 12/2016 | Fong et al. |

(Continued)

FOREIGN PATENT DOCUMENTS

| CN | 103370004 A | 10/2013 |
| CN | 106470598 A | 3/2017 |

(Continued)

OTHER PUBLICATIONS

Random Forests, Breimann, L., Machine Learning, 45, pp. 5-32, Kluwer Academic Publishers, 2001.

(Continued)

*Primary Examiner* — Charles Cai
(74) *Attorney, Agent, or Firm* — McGlew and Tuttle, P.C.

(57) ABSTRACT

A process for analyzing multidimensional vector data of a motion sensor for detecting a breathing motion, includes receiving and storing the multidimensional vector data of the motion sensor in a time series, calculating a plurality of medium-term vectors and of a plurality of long-term average vectors, calculating and storing a plurality of mean-free vectors depending on a difference between a respective medium-term vector and a respective long-term average vector and determining a plurality of unit vectors. The respective unit vector is oriented in a random direction. A plurality of scalar products are calculated from a respective mean-free vector and the unit vector assigned to the mean-free vector. A motion identification is calculated, which is an indicator of the breathing motion, based on the plurality of scalar products. An analysis signal is determined and output based on a comparison between the motion identification and a predefined motion threshold value.

18 Claims, 6 Drawing Sheets

(56) References Cited

U.S. PATENT DOCUMENTS

| | | |
|---|---|---|
| 9,510,775 B2 | 12/2016 | Morren et al. |
| 2004/0006375 A1 | 1/2004 | Poezevera |
| 2005/0113671 A1 | 5/2005 | Salla et al. |
| 2009/0062628 A1 | 3/2009 | Yamamoto et al. |
| 2010/0076061 A1 | 3/2010 | McCray et al. |
| 2011/0105915 A1 | 5/2011 | Bauer et al. |
| 2012/0065524 A1 | 3/2012 | Morren et al. |
| 2012/0296221 A1* | 11/2012 | Morren .............. A61B 5/113 600/534 |
| 2016/0183846 A1 | 6/2016 | Derkx |
| 2018/0344170 A1 | 12/2018 | Ganton et al. |

FOREIGN PATENT DOCUMENTS

| | | |
|---|---|---|
| TW | 201612845 A | 4/2016 |
| WO | 2011098944 A1 | 8/2011 |
| WO | 2015018752 A1 | 2/2015 |
| WO | 2018222291 A1 | 12/2018 |

OTHER PUBLICATIONS

Phan Duy Hung. "Estimating respiration rate using an accelerometer sensor" Proceedings of the 8th International Conference on Computational Systems—Biology and Bioinformatics, CSBIO 17, New York. New York. USA. Dec. 7, 2017. Revised Dec. 8, 2017 .* pp. 11-14.

Sajjad Hossain Hm et al. "An Active Sleep Monitoring Framework Using Wearables" ACM Transactions on Interactive Intelligent Systems (TIIS), ACM, 2 Penn Plaza, Suite 701 New York NY 10121-0701 USA, vol. 8, No. 3, Jul. 13, 2018 (Jul. 13, 2018), pp. 1-30.

Xiao Sun et al. "SleepMonitor: Monitoring Respiratory Rate and Body Position During Sleep Using Smartwatch" Proceedings of the ACM on Interactive, Mobile, Wearable and Ubiquitous Technologies, vol. 1, No. 3, Sep. 11, 2017 (Sep. 11, 2017), pp. 1-22.

NPL: A. Bates et al: Respiratory rate and flow waveform estimation from tri-axial accelerometer data.

* cited by examiner

PROCESS, PORTABLE DEVICE AND SYSTEM FOR ANALYZING VECTOR DATA

CROSS REFERENCE TO RELATED APPLICATIONS

This application is a United States National Phase Application of International Application PCT/EP2019/057974, filed Mar. 29, 2019, and claims the benefit of priority under 35 U.S.C. § 119 of German Application 10 2019 000 608.9, filed Jan. 30, 2019, the entire contents of which are incorporated herein by reference.

TECHNICAL FIELD

The present invention pertains to a process for analyzing multidimensional vector data of a motion sensor, as well as to a portable device for detecting a motion, especially for detecting a breathing motion. The present invention further pertains to a system for detecting a motion, especially for detecting a breathing motion, wherein the system comprises the portable device and a host device.

TECHNICAL BACKGROUND

Many processes for analyzing vector data of an acceleration sensor are known. Algorithms have become established in this connection in order to make it possible to infer predefined features of a motion of the acceleration sensor from vector data in a reliable manner.

In the area of motion detection, the U.S. Pat. No. 9,510,775 B2 describes the widely used method of principal component analysis for analyzing multidimensional vector data.

Furthermore, it is known that processes for the analysis of vector data can be used within the framework of a patient monitoring, for example, during the detection of an activity of a patient by an acceleration sensor.

SUMMARY

An object of the present invention is to provide an improved process for the analysis of multidimensional vector data, especially a process with an especially low computing power necessary for carrying out the process.

A process for analyzing multidimensional, especially three-dimensional vector data of a motion sensor, especially for detecting a breathing motion, is proposed according to the present invention to accomplish this object according to a first aspect of the present invention.

The process according to the present invention has the following steps:

Reception and storage of the multidimensional vector data of the motion sensor in a time series, especially at regular time intervals;

calculation of a plurality of medium-term vectors V1 by an averaging of the vector data received over a respective, predefined first time interval;

calculation of a plurality of long-term average vectors V2 by an averaging of the received vector data over a predefined second time interval, which is longer than the first time interval;

calculation and storage of a plurality of mean-free vectors V, depending on a difference between a respective medium-term vector V1 from a plurality of medium-term vectors and a respective long-term average vector V2 from the plurality of long-term average vectors, based on a time-dependent assignment between medium-term vectors V1 and long-term average vectors V2;

determination of a plurality of unit vectors E, wherein a respective unit vector is oriented in a random direction, and assignment of a respective unit vector E to a respective mean-free vector V;

calculation of a plurality of scalar products P, each from a mean-free vector V from the plurality of mean-free vectors V and from the unit vector E assigned to this mean-free vector V;

calculation of a motion identification, which is an indicator of a breathing motion, based on the plurality of scalar products P; and determination and outputting of an analysis signal based on a comparison between the motion identification and a predefined motion threshold value.

The present invention is based on the finding that the analysis and transmission of scalar values requires an especially small amount of computing power for a device implementing the process. Furthermore, it was found within the framework of the present invention that the influence of the force of gravity on the motion sensor must be subtracted from the data obtained for a motion detection, for example, for the detection of a breathing motion. This is achieved according to the present invention by the unit vectors oriented in respective random directions and by the random projections of the mean-free vectors, which projections are obtained thereby. Features that are rotation invariant to a spatial orientation can be extracted by these from the plurality of scalar products.

The process according to the present invention especially advantageously makes possible the processing of multidimensional vector data by an analysis of scalar quantities. Processing steps requiring a great computing effort, as they are necessary, for example, in principal component analysis, are avoided hereby. This leads, furthermore, to a reduced storage effort for a device carrying out the process.

The low computing effort needed for the process according to the present invention leads, furthermore, to a low power consumption and hence to a small battery size and/or to a longer battery life. A smaller size of the corresponding device and/or a longer mobile use time of the device are advantageously made possible hereby.

The determination of the analysis signal based on the comparison between the motion detection and the predefined motion threshold value makes it advantageously possible to carry out a final analysis of the vector data even without computation processes requiring a high computing effort, by a simple comparison of two scalar values. This additionally reduces the necessary computing effort and hence the necessary computing power to be provided for the process according to the present invention. This leads, in turn, to a low power consumption, which makes it possible to use a battery of a small size and/or to have a longer battery life.

The process according to the present invention advantageously combines a calculation of the motion identification, which requires a low computing power, with an analysis of the motion identification by a comparison operation, which likewise requires a low computing power.

The motion identification is an indicator of the breathing motion, which may be formed as a scalar value, but also as a plurality of values. The calculation of the motion identification consequently implies the calculation of features of a motion analyzed via the motion sensor.

The motion threshold value is typically an empirically determined value, which implies a weak breathing motion of a living being to be tested, especially of a person to be tested. For example, this may be a motion value characteristic of a breathing curve. Such a motion value is typically determined from a plurality of test series in order to set a threshold value, below which the presence of a breathing motion cannot be assumed with certainty any longer.

The reception and storage of the vector data in a time series means that a vector each with determined data of a measurement of the motion sensor is received and stored at predefined time intervals. The plurality of vectors received over time form the vector data according to the present invention.

The unit vector has a value of 1. The random direction is a randomly determined direction, especially randomly determined direction having equal distribution over all three dimensions in space. Algorithms for determining a random direction are known and will not be explained in more detail below.

The averaging over the first and second time intervals is carried out everywhere on the basis of a plurality of vectors of the multidimensional vector data, which were received within the corresponding time interval. The predefined time intervals, which form the time series, are consequently shorter than the first time interval and also shorter than the second time interval. It is advantageously ensured hereby that the respective long-term average vector V2 indicates a long-term tendency of a motion or position of the motion sensor implied by the vector data, whereas the respective medium-term vector V1 indicates a value of a motion implied by the vector data, which value is present for a short time interval. The long-term average vectors V2 and the medium-term vectors V1 thus represent each a sliding mean value, and averaging is carried out corresponding to the first time interval and to the second time interval over different run times of the sliding mean value. As a result, high-frequency components are advantageously filtered thereby out of the multidimensional vector data, which reflect only short-term measurement inaccuracies of the motion sensor.

Averaging is defined within the framework of the present invention as any kind of averaging. In particular, it may be an arithmetic averaging, a geometric averaging, a quadratic averaging, and a harmonic averaging. Furthermore, the averaging may be a multi-step averaging, especially a two-step or three-step averaging. Multi-step averaging means here that a first averaging of a plurality of groups of values takes place within a respective group and these averaged values are, in turn, averaged among one another in a next step.

Preferred embodiments of the process according to the first aspect of the present invention will be described below.

In a preferred embodiment, the multidimensional vector data are three-dimensional vector data. The three components of the vector data are formed here by the three directions in space. In another embodiment, the multidimensional vector data are two-dimensional vector data. The two components preferably correspond here to two directions in space. In yet another embodiment, the multidimensional vector data are four-dimensional vector data. The four components correspond here to the three directions in space and to time.

In an especially preferred embodiment, the determination of the analysis signal is based on a classification of the motion identification, which is based on a comparison of motion parameters induced by the motion identification with a plurality of respective motion threshold values. A comparison with a plurality of motion threshold values makes possible the analysis of a plurality of parameters of the motion detected via the vector data. The process according to this embodiment makes possible an especially precise classification of the motion identification. The motion identification is formed here preferably by a plurality of scalar values, for example, in the form of a matrix or in the form of a motion curve. The plurality of motion threshold values is typically a plurality of empirically determined values, which imply (indicate) a weak breathing motion. For example, this may be a plurality of motion values characteristic of a breathing curve. Such a plurality of motion values are typically determined from a plurality of test series in order to set threshold values, below which the presence of a breathing motion cannot be assumed with certainty any longer. In an especially preferred variant of this embodiment, the classification of the motion identification is based on a random forest algorithm. Compared to other known algorithms for classification, the random forest algorithm makes possible a classification with an especially low computing effort, because a classification of the motion identification is carried out only on the basis of a number of comparisons. A detailed description of the structure of a random forest algorithm is found, among other things, in the document "Random Forests," Breimann, L., Machine Learning, 45, pp. 5-32, Kluwer Academic Publishers, 2001.

In an especially preferred embodiment of the process according to the present invention, the analysis signal shows a motion of the motion sensor providing the vector data, which motion is caused by breathing. The fact that the process according to the present invention leads to a motion identification that is rotation invariant is advantageously utilized here. The motion caused by the breathing is likewise possible in all directions in space, so that the motion identification according to the present invention is especially advantageous for the detection of breathing. Furthermore, it is advantageously utilized in this embodiment that the combination of a feature extraction carried out by means of the motion identification and of a classification based on comparisons can lead to an especially accurate detection of a motion, so that even a small motion, as it can be assumed for breathing, can be detected. In a preferred variant of this embodiment, the analysis signal indicates whether breathing is present.

In another advantageous embodiment of the present invention, the calculation of the motion identification is based on a sum of squared scalar products. In a preferred variant of this embodiment, the calculation of the motion identification is based at least partially on the sum of the squares of the scalar products P. As a result, the motion identification advantageously shows an indicator of a kinetic energy of the motion detected by the motion sensor. In an especially preferred variant of this embodiment, the motion identification shows both the sum of the squares of the scalar products P and the scalar products P as an indicator of an amplitude of the detected motion.

In another advantageous embodiment, the calculation of the motion identification is also based, in addition to the plurality of scalar products, on the plurality of mean-free vectors V. As a result, an amplitude and/or direction of the motion to be analyzed can be directly inferred from the multidimensional vector data.

The time-dependent assignment between medium-term vectors V1 and long-term average vectors V2 is carried out in an advantageous embodiment such that the first time interval used for the calculation of the respective medium-term vector V1 is essentially within the second time interval used for the calculation of the respective long-term average vector V2. As a result, a respective mean-free vector V from the plurality of mean-free vectors V induces a motion amplitude because the current, long-term motion tendency in the form of the long-term average vector V2 is subtracted from the currently present medium-term vector V1. In a preferred variant, the first time interval is completely within the second time interval, especially centrally within the second time interval. It is ensured hereby that the long-term average vector V2 indicates the long-term motion tendency present over time during the determination of the data for the medium-term vector V1.

In an advantageous embodiment, the second time interval is at least twice as long as the first time interval, preferably at least four times as long as the first time interval, and especially preferably at least six times as long as the first time interval. The first time interval advantageously has a duration of at least 0.2 sec, preferably at least 0.5 sec and especially preferably at least 1 sec.

In another preferred embodiment, the process for analyzing sensor data comprises, after the reception and storage of the multidimensional vector data, in an additional process step, an activity detection based on the multidimensional vector data, and the further process steps are only carried out when an activity parameter arising from the activity detection is lower than a predefined activity threshold value. In a variant of this embodiment, the outputted activity parameter is formed by a component or a vector value of the multidimensional vector data. It is advantageously ensured in this embodiment that the precise process according to the present invention for analyzing vector data is used only if no motion is indicated by a process for activity detection, which process involves a markedly lower computing effort. The computing effort of the process according to the present invention is advantageously reduced further hereby. Furthermore, it can be ensured hereby that an incorrect analysis concerning a breathing motion is not outputted as an analysis signal due to an activity of a tested living being. The predefined activity threshold value is typically an empirically determined value, which implies at least a weak motion of limbs of the living being tested. Such a value is typically determined from a plurality of test series in order to set a threshold value, below which the presence of an at least weak motion of the limbs cannot be assumed with certainty any longer. In a variant of this embodiment, the activity detection is carried out by a determination of the variation of the detected multidimensional vector data and the subsequent comparison with the predefined activity threshold value. This will be discussed in detail within the framework of the description of FIG. 2.

In a preferred embodiment of the process according to the present invention, the process has, furthermore, a selection of the motion threshold value or of a plurality of motion threshold values used for the determination of the analysis signal from a predefined group of motion threshold values, the selection depending on an analysis of a component of the multidimensional vector data, especially of an output signal of the detection of a prone position. In an especially preferred variant of this embodiment, the plurality of motion threshold values is used in a random forest algorithm. Motion threshold values that are especially suitable for a position of the motion sensor that arises from the analysis of the component can advantageously be used in this embodiment. It is especially advantageously detected in a variant of this embodiment whether the living being to be tested is right now in a prone position or not, and the motion threshold value or the plurality of motion threshold values are selected independently from this. The predefined group of motion threshold values is stored in a variant of this embodiment on an external device, so that this variant further comprises the process steps that a selection signal is outputted depending on the analysis of the component and the motion threshold value or the plurality of motion threshold values are outputted and received based on the selection signal.

In an advantageous variant of the preceding embodiment, the selection depends on an analysis of a z component of the multidimensional vector data, wherein the z component is to be oriented during a beginning of a data recording by the motion sensor essentially in the direction of the force of gravity acting on the motion sensor, and wherein the analysis of the z component is based on a comparison between an acceleration force acting on the z component and a predefined acceleration threshold value oriented according to the force of gravity. It can be determined by the comparison between the acceleration force acting on the z component and the force of gravity whether the z component is still always oriented in the direction of the force of gravity or whether a change in the position of the motion sensor has occurred since the beginning of the data recording. In particular, a prone position of the living being to be tested can be detected. The motion sensor is preferably an acceleration sensor in this embodiment. In a variant of this embodiment, the acceleration threshold value is in a range between 0 m/sec2 and −5 m/sec2, especially between −0.2 m/sec2 and −2 m/sec2, especially preferably between −0.7 m/sec2 and −1 m/sec2. The comparison between the acceleration force acting on the z component and the force of gravity is preferably carried out by a comparison with a value averaged for the acceleration force over a corresponding time interval. The mean value is an exponential mean value in one example.

To accomplish the object of the present invention, a portable device for detecting a motion, especially for detecting a breathing motion, with a fastening device, with a motion sensor, with a preprocessing unit and with a transmitter unit is proposed according to a second aspect.

The fastening device is configured to fasten the portable device to an article of clothing of a user.

The motion sensor is configured to generate, depending on a motion of the portable device, multidimensional vector data, which indicate a direction and an amplitude of the motion of the portable device, and to output these multidimensional vector data in a time series.

The preprocessing unit is connected for signal technology to the motion sensor and is configured to receive the multidimensional vector data and to store them in a storage module of the preprocessing unit, and it is further configured to calculate a plurality of medium-term vectors V1 by an averaging of the received vector data, a respective predefined first time interval, which is longer than the reception time intervals, to calculate a plurality of long-term average vectors V2 by an averaging of the received vector data over a predefined second time interval, which is longer than the first time interval, to calculate a plurality of mean-free vectors V depending on a difference between a respective medium-term vector V1 from the plurality of medium-term vectors and a respective long-term average vector V2 from the plurality of long-term average vectors based on a time-dependent assignment between medium-term vectors V1 and long-term average vectors V2 and to store them in the storage module, to determine a plurality of unit vectors E, wherein a respective unit vector E is oriented in a random direction, and to assign a respective unit vector E to a respective mean-free vector V, and wherein the preprocessing unit is further configured to calculate a plurality of scalar products P each from a mean-free vector V from the plurality of mean-free vectors and from the unit vector E assigned to this mean-free vector V.

The transmitting unit is connected to the preprocessing unit at least indirectly for signal technology and is configured to transmit a motion signal, which is based on the plurality of scalar products P.

The portable device advantageously makes possible the preprocessing of multidimensional vector data, which requires an especially low computing power. This is made possible by the calculation and the use of scalar values, which can be carried out very rapidly by a processor of the preprocessing unit compared to complicated calculation algorithms, for example, a principal component analysis. This can support a comparatively low power consumption of the portable device.

The low power consumption makes possible a small battery size and/or a long battery life of a battery within the portable device. A small overall size of the portable device and/or an especially long mobile use time of the portable device is made possible hereby.

An additional unit is arranged between the preprocessing unit and the transmission unit in different embodiments according to the present invention of the portable device, so that the preprocessing unit is connected indirectly to the transmission unit for signal technology. The preprocessing unit is connected directly to the transmission unit in alternative or additional embodiments.

Preferred embodiments of the portable device according to the second aspect of the present invention will be described below.

The fastening device according to the present invention is typically configured to be fastened to the article of clothing of the user by means of a detachable connection. In one embodiment, the detachable connection is a magnetic connection, the article of clothing being arranged between two magnets of the magnetic connection. In another embodiment, the detachable connection is embodied by a pin. In another embodiment, the detachable connection is embodied by means of a clamp connection.

In an especially preferred embodiment, the portable device has, furthermore, an energy source, which is configured to supply the motion sensor, the preprocessing unit and the transmission unit with power. In an advantageous variant of this embodiment, the energy source is a replaceable battery.

In another, especially preferred embodiment, the motion sensor is configured as an acceleration sensor. The configuration of an acceleration sensor is known and will not therefore be described in detail below.

In another embodiment of the portable device according to the present invention, the preprocessing unit is further configured to calculate a motion identification, which is an indicator of a breathing motion, based on the plurality of scalar products P. The motion signal can especially advantageously transmit a small amount of data in this embodiment, because only the motion identification must be outputted to an external device for the analysis of the multidimensional vector data. The motion identification comprises at least one feature of the multidimensional vector data, which is obtained from the plurality of scalar products P.

In an especially advantageous variant of the above embodiment, the portable device has, furthermore, a classification unit, which is connected to the preprocessing unit for signal technology, and which is configured to determine an analysis signal based on a comparison between the motion identification and a predefined motion threshold value and to output it to the transmission unit. In an advantageous example of this variant, the preprocessing unit is connected to the transmission unit for signal technology indirectly via the classification unit. In an especially advantageous example of this variant, motion parameters induced by the motion identification are compared with a plurality of respective motion threshold values. This comparison is based especially advantageously on a random forest algorithm. This variant of the embodiment is especially advantageous due to the fact that only the result of the comparison between motion identification and motion threshold value is transmitted as a motion signal by the transmission unit. The motion signal has an especially simple configuration as a result, so that errors in the transmission by the transmission unit can be avoided.

The selection of a motion threshold value or of a plurality of motion threshold values preferably depends on an analysis of a component of the multidimensional vector data by the preprocessing unit, especially on an output signal of a prone position detection. As a result, the motion threshold values especially suitable for the current position of the motion sensor can advantageously be used by the classification unit.

In another embodiment of the portable device according to the second aspect of the present invention, the preprocessing unit carries out the calculation of the medium-term vectors V1 and of the long-term average vectors V2 and the subsequent steps only if an activity parameter, which was outputted by the activity detection, is lower than a predefined activity threshold value in a preceding processing step of the preprocessing unit, which step comprises an activity detection based on the multidimensional vector data.

To accomplish the object according to the present invention, a system for detecting a motion, especially for detecting a breathing motion, which has the portable device according to at least one of the above embodiments of the second aspect of the present invention and a host device, is proposed according to a third aspect of the present invention.

The host device is configured to receive the motion signal transmitted by the transmission unit and to output an optical and/or acoustic output signal based on the motion signal via an output unit of the host device, wherein the output signal implies a motion of the portable device, which said motion is implied by breathing.

The system according to the present invention advantageously makes it possible to output an analysis of the multidimensional vector data by a person located at a spaced location from the portable device via the host device. A part of the computing power necessary for the analysis of the multidimensional vector data is advantageously provided hereby by a processing unit within the host device.

Furthermore, the system according to the present invention makes it possible to connect a plurality of portable devices to a host device and/or the portable device to a plurality of host devices. For example, an especially clear analysis of vector data of a plurality of users of portable devices, especially a simultaneous detection of the breathing motion of a plurality of persons can be carried out hereby.

Preferred embodiments of the system according to the third aspect of the present invention will be described below.

The transmission of the motion signal by the transmission unit to the host device preferably takes place in a wireless manner, for example, by a Bluetooth, ZigBee, WLAN, NFC or DECT connection, or by another wireless connection.

The host device may be a stationary device, for example, a multifunctional medical device, or a device intended for mobile use, for example, a mobile wireless device, a notebook, a smartwatch or a tablet PC.

In one embodiment of the system according to the present invention, the output signal comprises the information on whether a motion caused by the breathing is present. In another embodiment, the output signal additionally comprises an amplitude and/or intensity of the breathing motion. In another embodiment, the output signal comprises an indication of the time at which a breathing motion was last detected. In another embodiment, the output signal comprises a duration of the breathing motion detected up to that point in time. An interim interruption of the breathing motion of a user of the host device can be reconstructed hereby.

In another embodiment of the system according to the third aspect of the present invention, the host device has, furthermore, a classification unit, which is configured to determine the plurality of scalar products P from the motion signal, to calculate a motion identification based on the plurality of scalar products P, and to determine and to output an analysis signal based on a comparison between the motion identification and a predefined motion threshold value, the optical and/or acoustic output signal being dependent on the analysis signal. In this embodiment, the host device advantageously assumes the classification of the multidimensional vector data preprocessed by the preprocessing unit within the portable device. The power consumption of the portable device can be further reduced hereby, as a result of which a longer run time of the energy supply unit of the portable device and/or a smaller size of the energy supply unit and hence a smaller size of the portable device are made possible. A host device equipped with a classification unit is preferably combined for the system according to the present invention with a portable device, which has no classification unit of its own. A multiple classification within the system is avoided hereby.

In another advantageous embodiment of the system according to the present invention, the determination of the analysis signal is based on a classification of the motion identification, which is based on a comparison of motion parameters induced by the motion identification with a plurality of respective motion threshold values, especially on a random forest algorithm. In an especially advantageous variant of this embodiment, the plurality of respective motion threshold values comprise a predefined plurality of motion threshold values, which are stored in an external storage device outside the system, and wherein the host device has, furthermore, a polling unit, which is configured to poll, to receive and to make available to the classification unit the plurality of motion threshold values at the external storage device via a wireless connection between the storage device and the polling unit. The external storage device may be, for example, an external server of a network, which can be accessed by the host device. The need to store large amounts of data on the host device is avoided in this variant. Thus, the variant according to the present invention advantageously makes it possible that the predefined quantity of motion threshold values is downloaded once on the external storage device, such that all host devices according to the present invention can access the preferably one external storage device.

The present invention shall now be explained in more detail on the basis of advantageous exemplary embodiments shown schematically in the figures.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
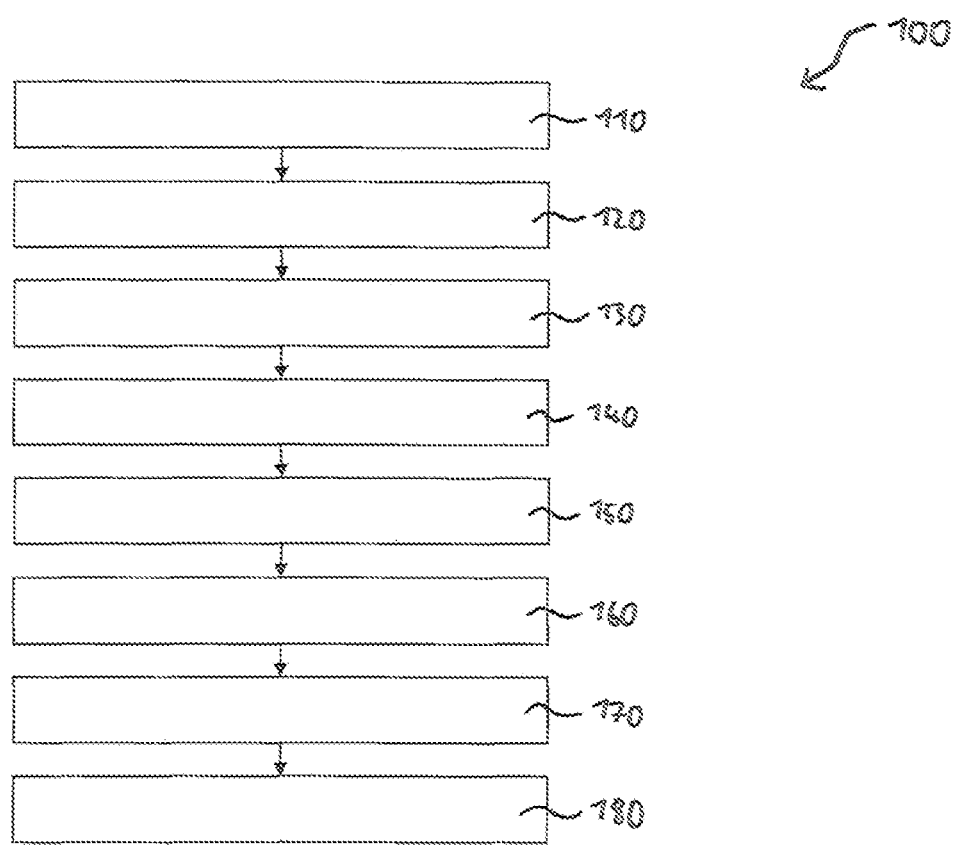
FIG. 1 is a flow chart of a first exemplary embodiment of a process according to the first aspect of the present invention.

Referring to the drawings, FIG. 1 shows a flow chart of a first exemplary embodiment of a process 100 according to the first aspect of the present invention.

The process 100 according to the present invention is a process for analyzing multidimensional vector data of a motion sensor, especially for detecting a breathing motion. The process 100 has the steps described below.

A first step 110 comprises a reception and storage of the multidimensional vector data of the motion sensor in a time series.

Another step 120 comprises a calculation of a plurality of medium-term vectors V1 by an averaging of the vector data received over a respective predefined first time interval.

A next step 130 comprises a calculation of a plurality of long-term average vectors V2 by an averaging of the vector data received over a predefined second time interval, which is longer than the first time interval.

A next step 140 comprises a calculation and storage of a plurality of mean-free vectors V as a function of a difference between a respective medium-term vector V1 from the plurality of medium-term vectors and a respective long-term average vector V2 from the plurality of long-term average vectors based on a time-dependent assignment between medium-term vectors V1 and long-term average vectors V2.

A next step 150 comprises a determination of a plurality of unit vectors E, wherein a respective unit vector is oriented in a random direction, and an assignment of a respective unit vector E to a respective mean-free vector V.

Another step 160 comprises a calculation of a plurality of scalar products P from a respective medium-term vector V from the plurality of mean-free vectors V and the unit vector E assigned to this mean-free vector V.

A next step 170 comprises a calculation of a motion identification, which is an indicator of the breathing motion, based on the plurality of scalar products P.

A final step 180 comprises a determination and outputting of an analysis signal based on a comparison between the motion identification and a predefined motion threshold value.

The steps of the process 100 are carried out typically partially simultaneously with one another. The multidimensional vector data are thus received and stored time and time again over a certain observation period, for example, during a sleep phase of a person being tested, while the medium-term vectors V1 and the long-term average vectors V2 are always also calculated further over the entire observation period in order finally to output the analysis signal at certain time intervals during the observation period based on a current motion identification. The analysis of multidimensional vector data is thus carried out according to the present invention by repeatedly carrying out the steps of the process 100 continuously over the observation period.

In the exemplary embodiment shown, the multidimensional vector data are received at a frequency between 10 Hz and 50 Hz, especially between 20 Hz and 40 Hz, in this case at about 26 Hz. The first time interval has a length between 0.8 sec and 2 sec, preferably between 0.8 sec and 1.5 sec, in this case about 1 sec. The second time interval has a length between 2 sec and 6 sec, especially between 3 sec and 4 sec, and about 3.7 sec in this case in the exemplary embodiment shown. The first time interval is always within the second time interval in each calculation.

The analysis signal indicates in the first exemplary embodiment shown whether it arises from the calculated motion identification that breathing of the patient being tested is present. In one exemplary embodiment, not shown, the analysis signal indicates, furthermore, since when an uninterrupted breathing was measured. In another exemplary embodiment, not shown, the analysis signal indicates how high the detection amplitude of the motion of the motion sensor, especially the breathing motion, is.

In the first exemplary embodiment, the calculated motion identification is based on a sum of squares of the scalar products P, this sum having the scalar products P that were calculated within a current identification time interval. As a result, the sum is an indicator of an energy of the motion detected by the motion sensor. Further, the motion identification has the mean-free vectors V calculated and stored within the current identification time interval in the exemplary embodiment shown. These vectors form an indicator of the amplitude of a currently detected motion of the motion sensor. In one exemplary embodiment, not shown, these currently calculated mean-free vectors are processed further for calculating the motion identification by forming another sliding mean value or by taking a predefined percentage of the mean-free vectors specifically into account, e.g., every fourth mean-free vector.

In another exemplary embodiment, not shown, the calculation of the motion identification is based on a processing of the calculated vectors by means of Fourier transformation, for example, by an implementation of the known Cooley-Tukey algorithm.

The determination of the analysis signal is based in the exemplary embodiment shown on a classification of the motion identification. The classification is carried out by a comparison of motion parameters induced by the motion identification with a plurality of respective motion threshold values. This comparison is configured in detail as a so-called random forest classification. In one exemplary embodiment, not shown, the classification of the motion identification is carried out by a direct comparison of a motion parameter induced by the motion identification with a predefined motion threshold value.

The random forest classification is especially suitable for the process 100 according to the present invention, because data received by algorithmics based on comparisons can be processed especially rapidly and in an especially uncomplicated manner in order to make a decision at the end between two states, e.g., "breathing present" and "breathing not present."

In one exemplary embodiment of the process according to the present invention, which example is not shown, a post-processing of the calculated data is carried out prior to the output of the analysis signal in order to reduce the probability of error concerning a result communicated by the analysis signal. In particular, the information that no motion of the motion sensor or only a slight motion of the motion sensor was detected, i.e., that no breathing is probably present, is outputted in this exemplary embodiment only after a repeated detection of this result in order to avoid a false alarm.

Figure 2:
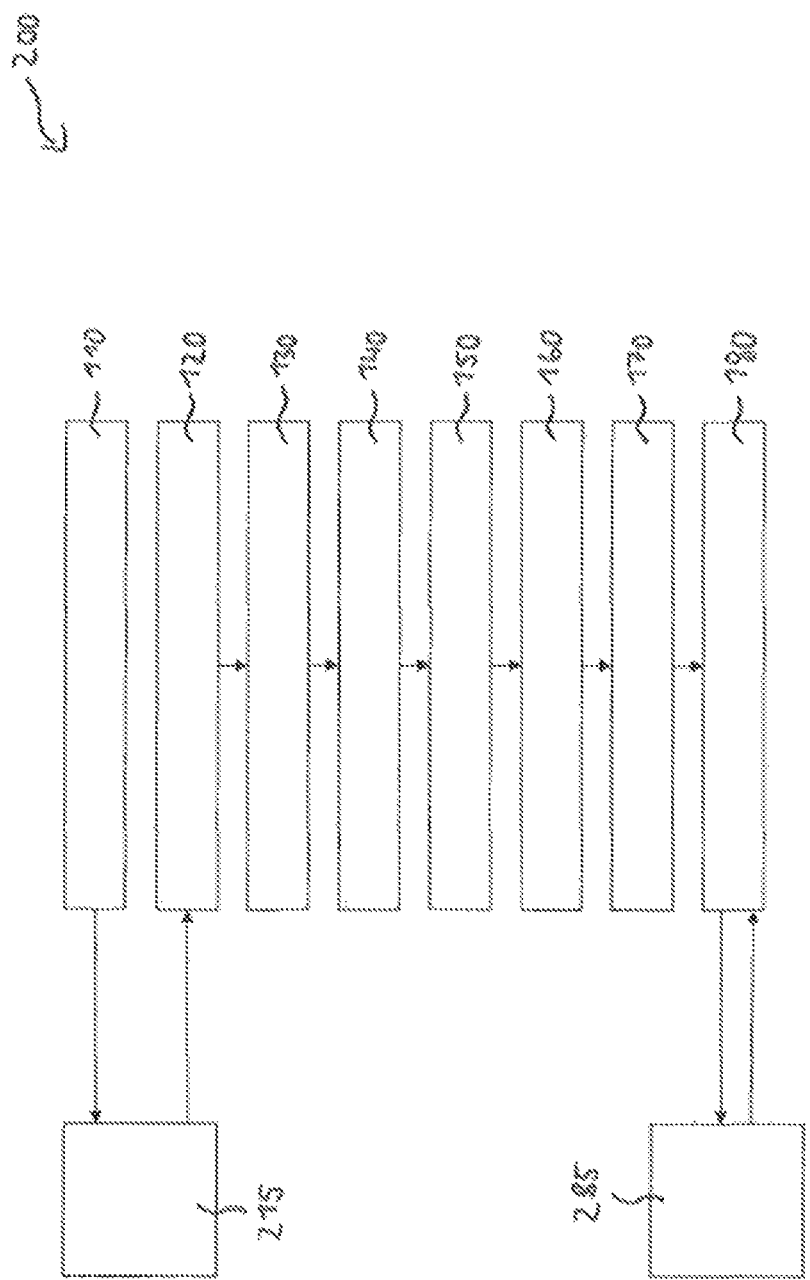
FIG. 2 is a flow chart of a second exemplary embodiment of a process according to the first aspect of the present invention.

FIG. 2 shows a flow chart of a second exemplary embodiment of a process 200 according to the first aspect of the present invention.

The process 200 differs from the process 100 shown in FIG. 1 in that step 120 is not carried out automatically after step 110, namely, after receiving and storing the multidimensional vector data. An activity detection is thus processed in an intermediate step 215.

An activity parameter is calculated within the framework of the activity detection and is finally compared to a predefined activity threshold value. The subsequent process steps are carried out only if the activity parameter is lower than the predefined activity threshold value, i.e., if an activity is determined that is lower than the activity that would be necessary to reach the activity threshold value. Such an advance checking is meaningful because a small motion, as it is present, for example, during the detection of breathing, could be superimposed by an excessively high activity, so that an incorrect analysis of the multidimensional vector data would be probable.

The vector data are accelerometer data in the exemplary embodiment described. These accelerometer data are used within the framework of the activity detection to determine a sliding mean value. The smoothing used in this connection by means of a sliding mean value is, for example, an exponential smoothing. A variation of the accelerometer data is determined by a comparison between the original accelerometer data and the sliding mean value. If this variation is greater than a predefined variation threshold value, a counter is set at a high value for a currently present activity time interval. Accelerometer data that are outside the simultaneous activity interval are not taken into account by the counter any longer. This counter forms the activity parameter for the respective activity time interval present. If this activity parameter exceeds a predefined activity threshold value, an activity signal, which indicates that an excessively high superimposed activity is currently present for the detection of a motion according to the present invention, is outputted in this exemplary embodiment. It can thus be outputted when a breathing motion is detected that it is not possible to detect whether a person is breathing because the person or his environment is moving too intensely for this.

Furthermore, process 200 differs from a process 100 shown in FIG. 1 by the further intermediate step 285.

A component of the multidimensional vector data is analyzed in step 285. Based on this analysis, the plurality of motion threshold values are selected from a predefined group of motion threshold values. In the exemplary embodiment shown, the analyzed component is the z component of the vector data, which is typically oriented at the beginning of an observation period in the direction of the force of gravity acting on the motion sensor. The vector data are, furthermore, accelerometer data, which are thus suitable for indicating a deviation from the gravitational acceleration typically acting in the direction of the force of gravity.

The analysis is carried out within the framework of step 285 for the exemplary embodiment shown such that two states are distinguished, namely, a z component, which is below a predefined acceleration threshold value, and a z component that is above the predefined acceleration threshold value. The acceleration threshold value is typically between 0 m/sec2 and −5 m/sec2 and it is in the range of −0.7 m/sec2 and −1 m/sec2 in this case. As a result, this analysis corresponds to a prone position detection, because a z component in the range of the negative gravitational acceleration, i.e., −9.81 m/sec2, is to be expected in the presence of a prone position.

The intermediate step 285 for the prone position detection is used in the exemplary embodiment shown only to determine suitable motion threshold values for carrying out the process according to the present invention. In one exemplary embodiment, not shown, a result of the prone position detection is likewise outputted by a corresponding signal, preferably by the analysis signal. In another exemplary embodiment, not shown, the prone position detection is inserted at another point of the process according to the present invention.

In another exemplary embodiment, not shown, the result of the activity detection is likewise outputted by means of the analysis signal.

Figure 3:
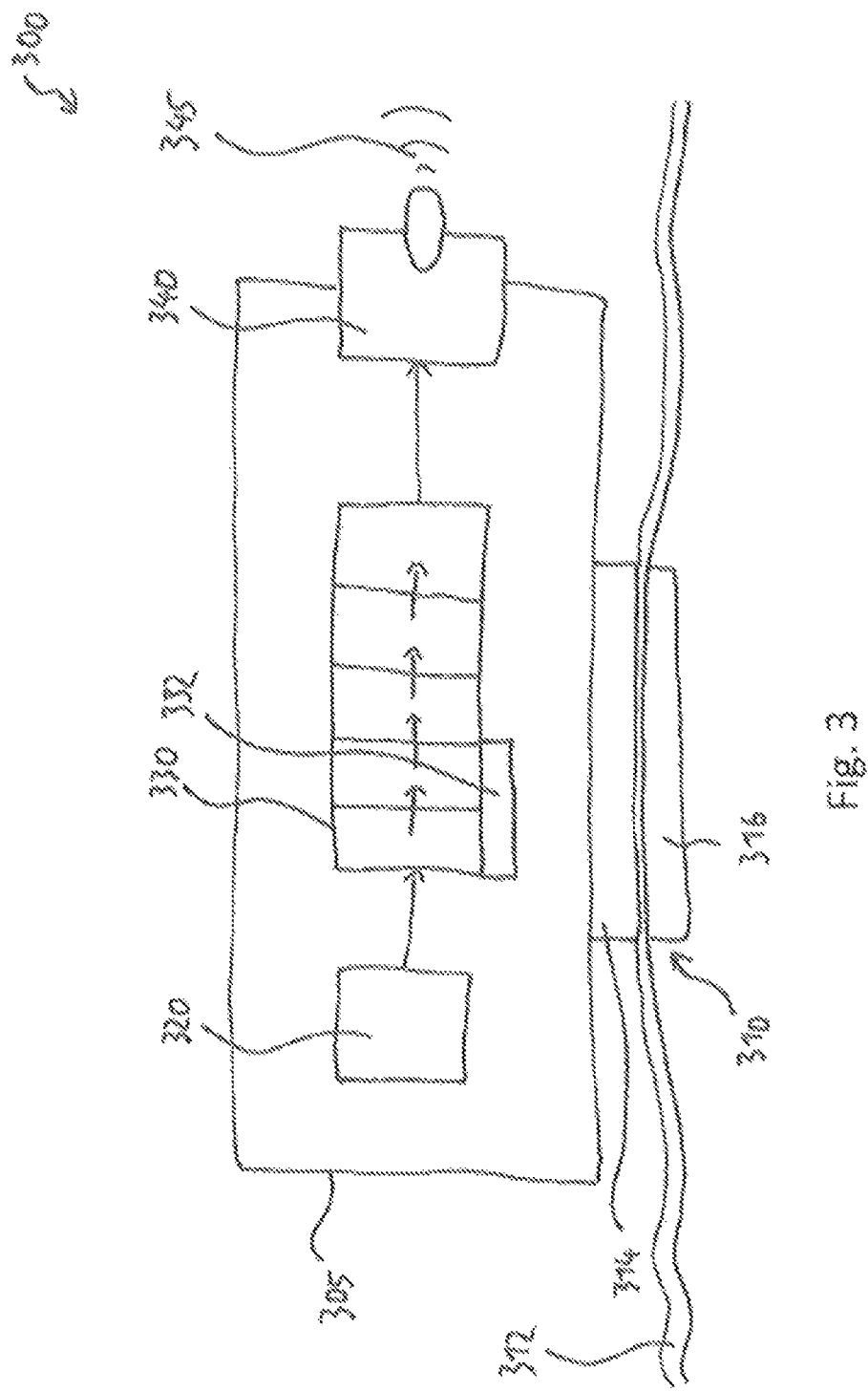
FIG. 3 is a schematic view of a first exemplary embodiment of a portable device according to the second aspect of the present invention.

FIG. 3 shows a schematic view of a first exemplary embodiment of a portable device 300 according to the second aspect of the present invention.

The portable device 300 is a device for detecting a motion, especially for detecting a breathing motion. The portable device 300 comprises here a fastening device 310, a motion sensor 320, a preprocessing unit 330 and a transmission unit 340.

The fastening device 310 is configured to fasten the portable device 300 to an article of clothing 312 of a user of the portable device 300. In the exemplary embodiment shown, the fastening device 310 is a magnetic connection, which comprises two parts 314, 316, wherein the first part 314 is fastened to a housing 305 of the portable device 300 and the second part 316 is arranged under the article of clothing 312 such that the magnetic interaction between the two parts 314, 316 holds the portable device 300 at the article of clothing 312.

In one exemplary embodiment, not shown, the fastening device forms a detachable connection, which can be embodied by means of a pin or by means of a clamp connection.

The motion sensor 320 is configured to generate, depending on a motion of the portable device 300, multidimensional vector data, which indicate a direction and an amplitude of the motion of the portable device 300, and to output these multidimensional vector data in a time series. The motion sensor 320 is an acceleration sensor in the exemplary embodiment shown.

The preprocessing unit 330 is connected to the motion sensor 320 for signal technology, in this case by a cable, and it is configured to receive the multidimensional vector data and to store them in a storage module 332 of the preprocessing unit 330.

Further, the preprocessing unit 330 is configured to calculate a plurality of medium-term vectors V1 by an averaging of the vector data received over a respective predefined first time interval, and to calculate a plurality of long-term average vectors V2 by an averaging of the vector data received over a predefined second time interval, which is longer than the first time interval.

The preprocessing unit 330 is configured, furthermore, to use the plurality of medium-term vectors V1 and the plurality of long-term average vectors V2 to calculate a plurality of mean-free vectors V as a function of a difference between a respective medium-term vector V1 and a respective long-term average vector V2. This calculation is based on a time-dependent assignment between medium-term vectors V1 and long-term average vectors V2. The time-dependent assignment is selected here to be such that the first time interval of a respective medium-term vector V1 is within the second time interval of a respective long-term average sector V2. Such a time-dependent assignment ensures that a respective mean-free vector V has an indicator of the amplitude of a detected motion. The plurality of mean-free vectors V is likewise stored by the preprocessing unit 330 in the storage module 332.

Further, the preprocessing unit 330 is configured to determine a plurality of unit vectors E, a respective unit vector E being oriented in a random direction, and to assign a respective unit vector E to a respective medium-term vector V. Since the unit vectors E are randomly selected vectors, no assignment instruction is necessary for the assignment between unit vector and mean-free vector V. In the present exemplary embodiment, the random direction is a direction selected randomly according to an equipartition in all directions in space. In one exemplary embodiment, not shown, another random distribution in all directions in space is used for the determination of the unit vectors. A determined unit vector always has just as many components as the vectors of the multidimensional vector data.

Corresponding to the assignment of a respective unit vector E and of a respective mean-free vector V, the preprocessing unit 330 is further configured to calculate a corresponding plurality of scalar products P from a respective mean-free vector V and from the associated unit vector E.

These scalar products P are used by the preprocessing unit 330 as the basis for transmitting a motion signal 345, which is based on the plurality of scalar products P, over an at least indirect connection for signal technology between the preprocessing unit 330 and the transmission unit 340. The at least indirect connection for signal technology is a direct connection via a cable in the exemplary embodiment shown. The motion signal 345 is transmitted in this case as a radio signal.

The different processing steps of the preprocessing unit 330 are indicated in FIG. 3 by different boxes within the preprocessing unit 330. This is an illustration, which illustrates the processing steps within a single processor of the preprocessing unit 330. In one exemplary embodiment, not shown, the processing steps of the preprocessing unit are divided between at least two preprocessing modules, which are separated in space.

The processing steps carried out within the preprocessing unit 330 may be carried out differently analogously to the exemplary embodiments discussed within the framework of FIG. 1 and FIG. 2 for the process according to the present invention.

In the exemplary embodiment shown, the motion signal 345 comprises the plurality of the scalar products P. In one exemplary embodiment, not shown, the motion signal comprises, in addition or as an alternative, a motion identification calculated on the basis of the scalar products P. In another exemplary embodiment, not shown, the motion signal additionally comprises the plurality of mean-free vectors V.

Figure 4:
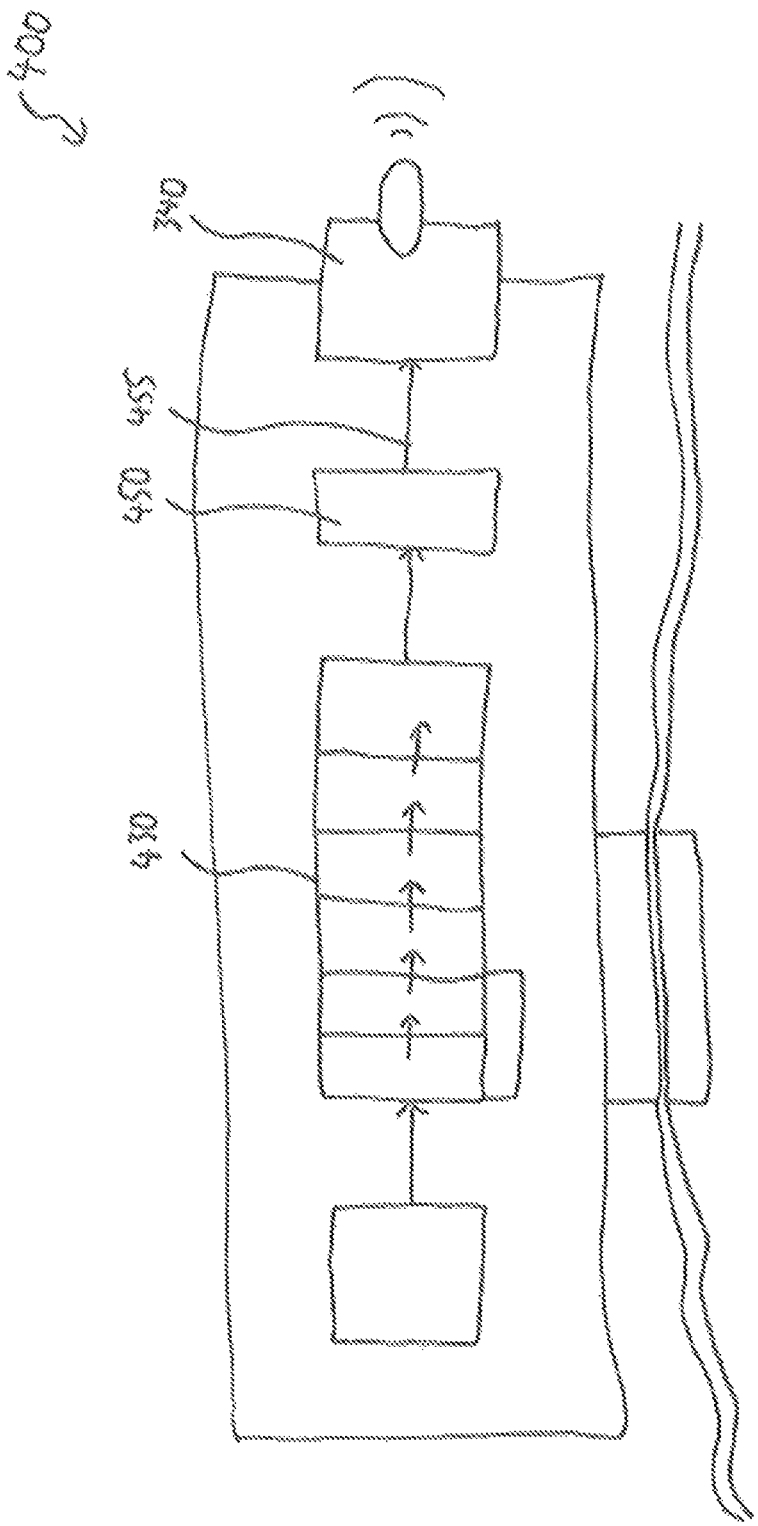
FIG. 4 is a schematic view of a second exemplary embodiment of a portable device according to the second aspect of the present invention.

FIG. 4 shows a schematic view of a second exemplary embodiment of a portable device 400 according to the second aspect of the present invention.

The portable device 400 differs from the portable device 300 shown in FIG. 3 in that a classification unit 450, which is connected to the preprocessing unit 430 and to the transmission unit 340 for signal technology, is arranged between the preprocessing unit 430 and the transmission unit 340.

The preprocessing unit 430 is additionally configured here to calculate the motion identification on the basis of the plurality of scalar products P. The motion identification comprises here a sum of squares of the scalar products P and an indicator of a current motion amplitude based on the plurality of mean-free vectors V.

The classification unit 450 is configured to determine an analysis signal 455 based on a comparison between the motion identification and predefined motion threshold values and to output it to the transmission unit 340. The transmission unit 340 transmits here the motion signal 345 based on the analysis signal 455 of the classification unit 450.

The comparison between motion identification and predefined motion threshold values as well as the selection of the predefined motion threshold values is carried out here within the framework of a random forest classification. In one exemplary embodiment, not shown, the motion threshold values are selected from a predefined group of motion threshold values, the predefined group of motion threshold values being stored in a memory of the classification unit.

The preprocessing unit 430 and the classification unit 450 form separate units in the exemplary embodiment shown. In one exemplary embodiment, not shown, both units are formed by a common processor.

Figure 5:
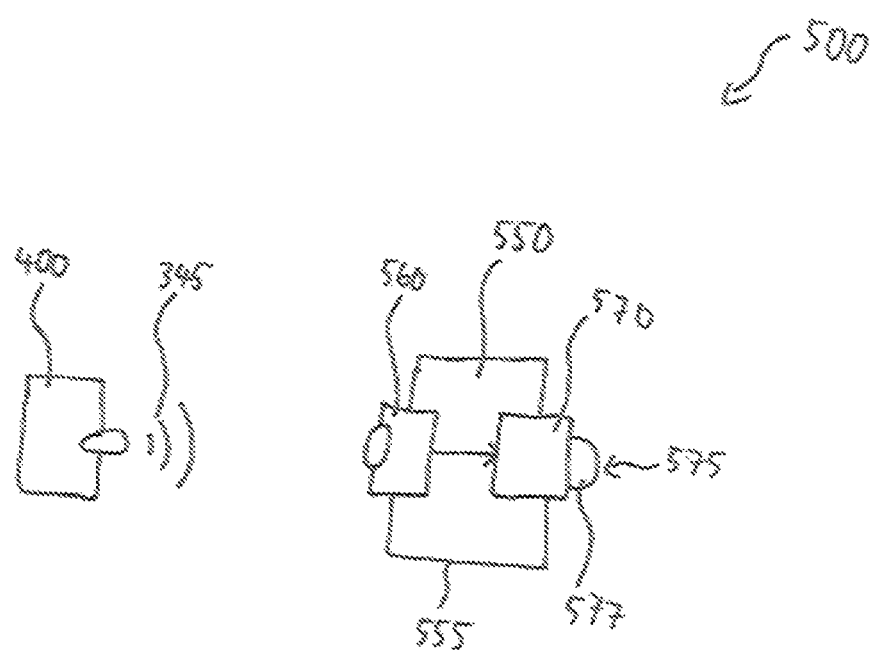
FIG. 5 is a schematic view of a first exemplary embodiment of a system according to the third aspect of the present invention.

FIG. 5 shows a schematic view of a first exemplary embodiment of a system 500 according to the third aspect of the present invention.

The system 500 according to the present invention is a system for detecting a motion, especially for detecting a breathing motion. It comprises the portable device 400 according to at least one exemplary embodiment according to the second aspect of the present invention and a host device 550.

The portable device is the portable device 400 shown in FIG. 4 in this case.

The host device 550 is configured to receive the motion signal 345 transmitted by the transmission unit via a receiving unit 560 and to output an optical and/or acoustic output signal 575 via an output unit 570 of the host device 550 on the basis of the motion signal 345. The output unit 570 has in this case an LED 577, whose optical output signal 575 is formed by the state of whether or not the LED 577 is illuminated or not. An illuminated LED 577 means here that no motion of the motion sensor, i.e., especially no breathing of the person being tested, was detected. A non-illuminated LED 577 indicates that breathing is being detected.

The host device 550 is a mobile device here with a housing 555 of its own. In one exemplary embodiment, not shown, the host device is a mobile telephone, a tablet PC, a notebook or a smartwatch.

The transmission between the portable device 400 and the host device 550 takes place here via a wireless connection, namely, a Bluetooth connection. In one exemplary embodiment, not shown, the transmission takes place via an alternative wireless connection, such as, e.g., an NFC, WLAN, ZigBee connection or another wireless connection.

Figure 6:
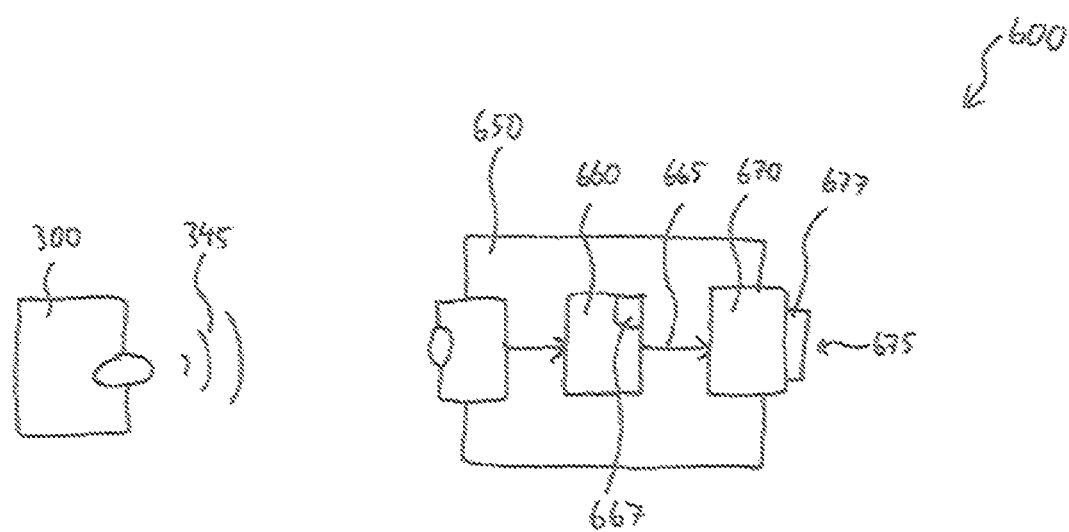
FIG. 6 is a schematic view of a second exemplary embodiment of a system according to the third aspect of the present invention.

FIG. 6 shows a schematic view of a second exemplary embodiment of a system 600 according to the third aspect of the present invention.

The system 600 according to the present invention differs from the system 500 shown in FIG. 5 in that the host device 650 also has a classification unit 660. Since the portable device 300 does not consequently need a classification unit, the device in question is the portable device 300 shown in FIG. 3 in the exemplary embodiment shown.

The motion signal 345 sent by the portable device 300 implies the plurality of scalar products P. The classification unit 660 is configured to determine the plurality of scalar products P from the motion signal 345 and to calculate a motion identification on the basis of the plurality of scalar products P. Furthermore, the classification unit 660 is configured to compare the motion identification to at least one motion threshold value and to output an analysis signal 665 based on this comparison. The output unit 670 is further configured to output the output signal 675 as a function of the analysis signal 665.

The classification is carried out in the exemplary embodiment shown by a comparison of motion parameters induced by the motion identification with a plurality of respective motion threshold values. The plurality of motion threshold values are selected and outputted corresponding to a random forest algorithm from a group of predefined motion threshold values, which are stored within a storage module 667 of the classification unit 660.

In one exemplary embodiment, not shown, the group of predefined motion threshold values is stored on an external storage device outside the system according to the present invention. The host device is configured, furthermore, in this exemplary embodiment to poll and to receive the plurality of motion threshold values via a polling unit of the host device and to provide them for the classification unit.

The output unit 670 has as the optical output for the output signal 675 a display 677, on which a result of the analysis of the vector data of the motion sensor is displayed.

The activity detection and the prone position detection explained within the framework of FIG. 2 are likewise embodied together or separately from one another in exemplary embodiments, not shown, of the portable device according to the second aspect of the present invention and of the system according to the third aspect of the present invention.

Features of the process according to the present invention may also be embodied, in principle, within processing steps of the portable device or of the system. In particular, advantages of the process according to the present invention cause the correspondingly operated portable device or the correspondingly operated system to have these advantages as well.

While specific embodiments of the invention have been shown and described in detail to illustrate the application of the principles of the invention, it will be understood that the invention may be embodied otherwise without departing from such principles.

The invention claimed is:

1. A process for analyzing multidimensional vector data of a motion sensor for detecting a breathing motion, the process comprising the steps of:
receiving and storing the multidimensional vector data of the motion sensor in a time series;
calculating a plurality of medium-term vectors by an averaging of the received vector data over a respective predefined first time interval;
calculating a plurality of long-term average vectors by averaging the received vector data over a predefined second time interval, which is longer than the first time interval;
calculating and storing a plurality of mean-free vectors as a function of a difference between a respective medium-term vector from the plurality of medium-term vectors and a respective long-term average vector from the plurality of long-term average vectors, based on a time-dependent assignment between the plurality of medium-term vectors and the plurality of long-term average vectors;
determining a plurality of unit vectors, wherein each respective unit vector is oriented in a random direction, and assigning the respective unit vector to a respective mean-free vector;
calculating a plurality of scalar products from a mean-free vector from the plurality of mean-free vectors and the unit vector assigned to this mean-free vector;
calculating a motion identification, which is an indicator of the breathing motion, based on the plurality of scalar products; and
determining and outputting an analysis signal based on a comparison between the motion identification and a predefined motion threshold value, wherein the breathing motion is monitored in real time according to the analysis signal.

2. A process in accordance with claim 1, wherein the determination of the analysis signal is based on a classification of the motion identification, which is based on a comparison of motion parameters induced by the motion identification with a plurality of respective motion threshold values.

3. A process in accordance with claim 2, wherein the classification of the motion identification is based on a random forest algorithm.

4. A process in accordance with claim 1, wherein the analysis signal indicates a motion of the motion sensor providing the vector data, wherein said motion is caused by breathing.

5. A process in accordance with claim 1, wherein the calculation of the motion identification is based on a sum of squares of the plurality of scalar products.

6. A process in accordance with claim 1, wherein the time-dependent assignment between the plurality of medium-term vectors and the plurality of long-term average vectors is carried out such that the first time interval used for the calculation of the respective medium-term vector is essentially within the second time interval used for the calculation of the respective long-term average vector.

7. A process in accordance with claim 1, wherein the process for analyzing sensor data comprises, after the reception and storage of the multidimensional vector data, an activity detection based on the multidimensional vector data in an additional process step, wherein the additional process step is carried out only if an activity parameter outputted by the activity detection is lower than a predefined activity threshold value.

8. A process in accordance with claim 1, further comprising selecting the motion threshold value or a plurality of motion threshold values from a predefined group of motion threshold values, which is used for the determination of the analysis signal, wherein the selection depends on an analysis of a component of the multidimensional vector data.

9. A process in accordance with claim 8, wherein the selection depends on an analysis of a z component of the multidimensional vector data, wherein the z component is to be oriented during a beginning of a data recording by the motion sensor in a direction of the force of gravity acting on the motion sensor, and wherein the analysis of the z component is based on a comparison between an accelerating force acting on the z component and a predefined acceleration threshold value oriented on the force of gravity.

10. A portable device for detecting a breathing motion, the portable device comprising:
a fastening device configured to fasten the portable device on an article of clothing of a user of the portable device;
a motion sensor configured to generate, depending on a motion of the portable device, multidimensional vector data, which indicate a direction and an amplitude of the motion of the portable device, and to output these multidimensional vector data in a time series;
a preprocessing unit connected to the motion sensor and configured:
to receive the multidimensional vector data and to store the multidimensional vector data in a storage module of the preprocessing unit,
to calculate a plurality of medium-term vectors by an averaging of the received vector data over a respective predefined first time interval,
to calculate a plurality of long-term average vectors by an averaging of the received vector data over a predefined second time interval, which is longer than the first time interval,
to calculate a plurality of mean-free vectors depending on a difference between a respective medium-term vector from the plurality of medium-term vectors and a respective long-term average vector from the plurality of long-term average vectors based on a time-dependent assignment between medium-term vectors and long-term average vectors and to store them in the storage module,
to determine a plurality of unit vectors, wherein a respective unit vector is oriented in a random direction, and to assign a respective unit vector to a respective mean-free vector, and
to calculate a plurality of scalar products from a mean-free vector from the plurality of mean-free vectors and the unit vector assigned to this mean-free vector; and
a transmission unit, which is connected to the preprocessing unit at least indirectly for signal technology, and which is configured to transmit a motion signal, which is based on the plurality of scalar products, wherein the breathing motion is monitored in real time according to the motion signal.

11. A portable device in accordance with claim 10, wherein the preprocessing unit is further configured to calculate a motion identification, which is an indicator of the breathing motion, based on the plurality of scalar products.

12. A portable device in accordance with claim 11, wherein the portable device further has a classification unit, which is connected to the preprocessing unit for signal technology, and which is configured to determine an analysis signal based on a comparison between the motion identification and a predefined motion threshold value and to output it to the transmission unit.

13. A system for detecting a breathing motion, the system comprising:
- a portable device comprising:
  - a fastening device configured to fasten the portable device on an article of clothing of a user of the portable device;
  - a motion sensor configured to generate, depending on a motion of the portable device, multidimensional vector data, which indicate a direction and an amplitude of the motion of the portable device, and to output these multidimensional vector data in a time series;
  - a preprocessing unit connected to the motion sensor and configured to receive the multidimensional vector data and to store the multidimensional vector data in a storage module of the preprocessing unit, to calculate a plurality of medium-term vectors by an averaging of the received vector data over a respective predefined first time interval, to calculate a plurality of long-term average vectors by an averaging of the received vector data over a predefined second time interval, which is longer than the first time interval, to calculate a plurality of mean-free vectors depending on a difference between a respective medium-term vector from the plurality of medium-term vectors and a respective long-term average vector from the plurality of long-term average vectors based on a time-dependent assignment between medium-term vectors and long-term average vectors and to store them in the storage module, to determine a plurality of unit vectors, wherein a respective unit vector is oriented in a random direction, and to assign a respective unit vector to a respective mean-free vector, and to calculate a plurality of scalar products from a mean-free vector from the plurality of mean-free vectors and the unit vector assigned to this mean-free vector; and
- a transmission unit, which is connected to the preprocessing unit at least indirectly for signal technology, and which is configured to transmit a motion signal, which is based on the plurality of scalar products; and
- a host device configured to receive the motion signal sent by the transmission unit and to output an optical and/or acoustic output signal via an output unit of the host device based one the motion signal, wherein the output signal implies a motion of the portable device, of which the motion is caused by breathing, wherein the breathing motion is monitored in real time according to the motion signal.

14. A system in accordance with claim 13, wherein the host device further comprises a classification unit configured to determine the plurality of scalar products from the motion signal, to calculate a motion identification based on the plurality of scalar products, and to determine and to output an analysis signal based on a comparison between the motion identification and a predefined motion threshold value, wherein the optical and/or acoustic output signal depends on the analysis signal.

15. A system in accordance with claim 14, wherein the determination of the analysis signal is based on a classification of the motion identification, which is based on a comparison of motion parameters induced by the motion identification with a plurality of respective motion threshold values.

16. A system in accordance with claim 15, wherein the plurality of respective motion threshold values comprise a predefined plurality of motion threshold values, which are stored in an external storage device outside the system, and wherein the host device further has a polling unit, which is configured to poll, to receive and to provide for the classification unit the plurality of motion threshold values at the external storage device via a wireless connection between the storage device and the polling unit.

17. A portable device in accordance with claim 12, wherein the classification of the motion identification is based on a random forest algorithm.

18. A system in accordance with claim 14, wherein the classification of the motion identification is based on a random forest algorithm.

* * * * *